United States Patent [19]
Boda et al.

[11] Patent Number: 5,406,214
[45] Date of Patent: Apr. 11, 1995

[54] METHOD AND APPARATUS FOR MEASURING MINORITY CARRIER LIFETIME IN SEMICONDUCTOR MATERIALS

[75] Inventors: János Boda; György Ferenczi; Péter Horváth; Zoltán Mirk; Tibor Pavelka, all of Budapest, Hungary

[73] Assignee: Semilab Felvezeto Fizikai Lab, RT, Budapest, Hungary

[21] Appl. No.: 808,671

[22] Filed: Dec. 16, 1991

[30] Foreign Application Priority Data

Dec. 17, 1990 [HU] Hungary .................. 43934/90

[51] Int. Cl.$^6$ ............... G01R 31/26; G01R 27/06
[52] U.S. Cl. .................. 324/765; 324/642; 324/752
[58] Field of Search ........... 324/158 D, 158 T, 158 R, 324/750, 751, 752, 765, 767, 642

[56] References Cited

U.S. PATENT DOCUMENTS

| | | | |
|---|---|---|---|
| 3,939,415 | 2/1976 | Terasawa | 324/158 R |
| 4,704,576 | 11/1987 | Tributsch et al. | 324/158 R |
| 4,949,034 | 8/1990 | Imura et al. | 324/158 D |
| 5,047,713 | 9/1991 | Kirino et al. | 324/158 R |
| 5,049,816 | 9/1991 | Moslehi | 324/158 T |
| 5,081,414 | 1/1992 | Kusama et al. | 324/158 D |
| 5,196,786 | 3/1993 | Usami et al. | 324/158 R |

OTHER PUBLICATIONS

PCT Internat'l. Search Report PCT/HU 91/00052 Dec. 17, 1991.
Microwave Techniques in Measurement of Lifetime in Germanium A. P. Ramsa et al, Journal of Applied Physics, vol. 30, No. 7, Jul. 1959.
The Study of Charge Carrier Kinetics in Semiconductors by Microwave Conductivity Measurements, M. Kunst et al, J. Appl. Phys. 60(10) 15 Nov. 1986.
History of Minority Carrier Lifetime Measurement Methods, Akira Usami, 3 Oct. 1988, pp. 1–8.

*Primary Examiner*—Ernest F. Karlsen
*Attorney, Agent, or Firm*—Flehr, Hohbach, Test, Albritton & Herbert

[57] ABSTRACT

A contactless apparatus for measuring contaminants in a semiconductor specimen (24) includes a tunable microwave generator (26) coupled by a coaxial cable (36) to a tuned narrowband microstrip antenna (38) that defines a through hole (72). The antenna is placed in near field relationship to the specimen to direct microwave energy toward a first specimen surface (44). This proximity provides a substantially more powerful microwave field than prior art systems, and the specimen comprises an impedance termination for the microwave path that includes the microwave generator and antenna, thereby rendering system measurements substantially immune to mechanical vibration of the specimen. A pulsed laser (42) directs optical energy through the antenna through hole toward the first specimen surface (44). The optical energy generates minority carriers within the specimen that begin to recombine upon cessation of each pulse. Minority lifetime decay affects microwave energy reflecting from freed holes and electrons in the specimen, which energy is coupled from the antenna to a detector (46) and preferably a computer system (48) that controls the system and provides signal processing of the detector output.

23 Claims, 4 Drawing Sheets

METHOD AND APPARATUS FOR MEASURING MINORITY CARRIER LIFETIME IN SEMICONDUCTOR MATERIALS

FIELD OF THE INVENTION

The invention relates generally to measuring carrier concentration in semiconductor materials, and more specifically to a method and apparatus for rapid measurement of minority carrier lifetime in semiconductor materials in a non-destructive, contact free manner.

BACKGROUND OF THE INVENTION

It is known in the art to determine the purity of semiconductor materials by examining the lifetime of minority carriers therein, in a non-destructive, contact free fashion. A typical prior art system for such measurements is disclosed in U.S. Pat. No. 4,704,576 to Tributsch, et al. (Nov. 3, 1987), and is generally depicted in FIG. 1. In such systems 2, the semiconductor specimen 4 to be tested is placed in a microwave field within or adjacent an open-ended waveguide system 6, between a microwave radiation source 8 (and related circulator 10) and a laser light source 12. Typically the microwave source 8 oscillates at about 10 GHz, with the microwave energy being carried by the waveguide system 6 one-half wavelength (1.5 cm) from the effective antenna 14 to and then from the specimen.

Waveguide system 6 and effective antenna 14 behave like an unterminated stripline antenna system that radiates microwave energy over a large area, without being able to concentrate energy on a given specimen area.

Usually the microwave source frequency is fixed, and the prior art system is tuned by mechanically moving a metal reflector (not shown) to change the microwave phase relationship until the reflected microwave signal (from the detector) is maximized. As shown in FIG. 1, many prior art systems subject one side 16 of the specimen to pulses of energy from the laser source 12, and subject the other specimen side 18 to microwave energy from the microwave source 8. This "two-sided" configuration has several drawbacks. In small resistivity specimens (e.g., <1 Ωcm), microwave penetration into the specimen is shallow, and thus the recombination phenomena within the specimen induced by the laser excitation at surface 16 is not adequately characterized by microwave energy at the specimen's other side 18. Even in prior art systems that are "one-sided" the inherent system microwave insensitivity hampers meaningful measurements for small resistivity specimens.

Another drawback of "two-sided" configurations as shown in FIG. 1 is that they prevent placing a non-oxidized specimen in an electrolytic bath during measurements. Such a bath serves to passivate non-oxidized specimen surfaces, substantially eliminating surface recombination effects that would otherwise dominate measurements.

The pulsed laser 12 bombards specimen side 16 with pulses of optical energy containing photons that create excess charge carriers within the specimen 4. Sufficient laser energy is present when the wavelength of the laser excitation exceeds the specimen bandgap. In a relatively high resistivity specimen, these carriers can affect the microwave energy reflected by the free electrons and holes in the crystal structure of the specimen. The reflected microwave energy is coupled via circulator 10 to a detector 20. The output from detector 20 allows measurement of the decay time of the optically generated excess carriers. This in turn enables a determination of the recombination time constant of such carriers within the specimen 4. By relatively incrementally repositioning the laser source 12 and specimen 4 in between measurements, the reflecting microwave energy may be used to map defects within the specimen.

More specifically, laser pulse photons that exceed the specimen's bandgap energy are absorbed into the specimen where they generate excess charge carriers, e.g., pairs of mobile electrons and holes that have excess concentrations $\Delta n$ and $\Delta p$. These excess carriers increase the specimen conductivity by $\Delta \sigma$:

$$\Delta\sigma = q(\mu_n \Delta n + \mu_p \Delta p)$$

where q is the electron charge, and $\mu_n$, $\mu_p$ are respectively the mobility of electrons and holes in the specimen. The excess carrier concentrations $\Delta n$ and $\Delta p$ decay over time as the carriers become trapped in defects or recombine along defects within the specimen. The excess carriers' time dependent concentration changes the microwave energy reflected from the free electrons and holes within the specimen, which changes are measured with detector 20 (and associated signal processing circuitry). Thus, a measurement of excess conductivity $\Delta \sigma$ is indicative of the defects and impurities within the specimen's crystal structure that affect the excess charge carriers.

In the simplest case, recombination is exponential with a reciprocal delay time ($1/\tau$) proportional to the concentration of recombination centers, or impurities. Thus $1/\tau$ (e.g., recombination lifetime) is a measure of the specimen quality.

Such measurements are especially suitable for materials such as Si that have indirect forbidden bands where the probability of band-band recombination is small. In such semiconductors, the recombination of electrically active impurities, precipitates, interface states formed around secondary phases, scatter centers (e.g., deviations from ideal periodicity) tend to decrease the excess carrier recombination lifetime.

While such prior art systems permit a non-destructive, contactless examination of minority carrier lifetime to provide information as to crystal defects present in the specimen, there are many shortcomings.

A first deficiency arises because microwave energy is coupled to and from the specimen via an open broad-beam waveguide over a relatively large distance (e.g., one-half wavelength). These distances and the broad-beam nature of the waveguide cause a substantial loss in microwave sensitivity, and such prior art systems are characterized by a poor signal/noise ratio. To compensate for such insensitivity, the laser source must be operated at fairly high energy levels. This restriction precludes using high and low laser energy levels for injection spectroscopic measurements to help determine the chemical nature of contaminants in the specimen. This first deficiency is especially troublesome where relatively small resistivity specimens are to be measured.

A second deficiency arises because the relatively large distances in the prior art systems creates standing waves within the microwave waveguide. This causes the specimen to become a tuning element dielectric that, unfortunately, detunes the system with the slightest specimen vibration. As a result, the system requires "resting" after each repositioning of the specimen relative to the laser, to allow the vibrations to dampen before new meaningful measurements can be taken. This "rest time" slows down the rapidity with which measurements may be taken, and complicates the rapid automatic relative repositioning of the specimen and laser source between measurements.

Finally, locating the specimen between the laser and microwave energy sources, as shown in FIG. 1, precludes placing the specimen in an electrolytic bath during measurement. This deficiency arises because an electrolyte bath would attenuate the depth of microwave penetration into side 18 of the specimen such that areas subject to laser illumination from the opposite side 16 are not reached. For a non-oxidized specimen, it would of course be advantageous to permit such testing because an electrolyte would passivate each specimen surface, thereby preventing surface recombination speed from dominating the system measurements. The result, unattainable in prior art configurations such as FIG. 1, would be measurement data providing truer insight as to the condition within the specimen. Of course a non-oxidized specimen could be annealed, typically at elevated temperatures of about 1100° C., to form an oxide layer, which would prevent surface recombination effects from dominating the measurements. However it is well known that such elevated temperatures can produce change in the specimen characteristics.

Thus, there is a need for a non-destructive, contact-free system to characterize semiconductor material that provides high measurement sensitivity, good signal/noise ratio, and permits injection spectroscopic measurements over a wide dynamic range of laser excitation energy. Such system should include a simple mechanism to achieve microwave frequency tuning to optimize system performance.

Further, there is a need for such a system that is substantially immune to specimen vibration, thereby shortening the time between measurements, allowing measurements to be made more rapidly.

Finally, such a system should allow positioning a non-oxidized specimen in an electrolyte bath to allow surface passivation during measurement, thereby permitting a more accurate characterization of the internal structure of the specimen.

The present invention discloses a method and apparatus providing such a system.

SUMMARY OF THE INVENTION

The present invention provides a non-destructive contactless system for determining minority carrier recombination lifetime in a semiconductor specimen. The invention includes a tuned source of microwave energy, a circulator and isolator, a preferably narrow bandwidth directional tuned microstrip antenna, a pulsed source of laser optical excitation, a detector and related circuitry, and means for repositioning the specimen relative to the laser source. Preferably the present invention further includes a computer system to coordinate operation of microwave source and laser excitation, positioning of the specimen, and processing of measured data from the detector and related circuitry.

Unlike the prior art wherein microwave energy is coupled to the specimen over a relatively long open channel tuned cavity that approximates an unterminated stripline antenna with a flat frequency response, the present invention makes the specimen an impedance termination in the microwave path. More specifically, microwave energy is coupled via coaxial cable from a tunable microwave generator to a preferably narrowband tuned microstrip antenna operating in near field. By near field, it is meant that the antenna is situated substantially less than one microwave wavelength from the specimen, preferably less than about 0.1 microwave wavelength, or about 2 mm. An antenna according to the present invention is frequency selective, and is optimized for the typically 10 GHz microwave frequency range, the exact system frequency being determined by the microwave generator frequency. The near field configuration in the present invention also subjects the specimen to a substantially greater microwave field intensity than prior art systems. This in turn provides microwave energy sensitivity substantially greater than known systems, thus making the present invention especially well suited for measurements of low resistivity specimens.

In further contrast to many prior art systems, the present system operates "one-sided", subjecting the same side of the specimen to the microwave energy and to the laser optical excitation. Preferably the system configuration is such that at the specimen surface, the effective microwave spot is not more than about sixty-four times larger than the effective laser beam spot, e.g., the microwave spot diameter is about eight times the laser beam spot diameter. Because the same side of the specimen is subjected to microwave and laser energy, the specimen may be positioned in an electrolyte bath during measurement. This allows surface passivation for a non-oxidized specimen, and thus permits a more accurate characterization of the internal structure of the specimen.

In still further contrast with the prior art, in the present invention the microwave frequency is readily tuned to optimize system sensitivity (e.g., to maximize detected reflected microwave power in response to specimen resistivity change). The tuned narrowband microstrip antenna further facilitates optimizing the microwave frequency to the specimen under examination. Varying the system frequency does not require the presence of reflectors or the like within the microwave field, and in fact the present invention renders the microwave field essentially insensitive to the precise position of objects therein, including the specimen. To further minimize detuning of the microwave system, the present invention maintains and controllably reposition the specimen using a robotic arm that is made of the same material (e.g., plexiglass, Teflon) as the staging or holding table whereon the robotic arm is located. So constructed, the microwave field experiences essentially a homogeneous environment.

Because of the near field configuration used, a specimen in the present invention is not a tuning element in an open cavity (as in the prior art). The configuration advantageously renders the present invention substantially immune to mechanical vibrations by the specimen. This immunity allows substantially more measurements to be accomplished within a given time because it is unnecessary to waste time between measurements to allow mechanical vibrations of the specimen to decay.

Finally, because the present invention preferably operates the antenna in near field, the effective microwave field at the specimen is about one-hundred times greater than in a prior art system. This coupled with the ease of optimizing the microwave frequency substantially improves the signal/noise ratio and allows the laser source to operate over a substantial dynamic power range, e.g., 1,000:1, thereby facilitating injection spectroscopic measurements. The ability of the present invention to provide meaningful measurements with laser excitation varying from about 25 W to about 25 mW is in stark contrast to prior art systems where microwave insensitivity precludes measurements with less than several watts of laser excitation.

In operation, a first side of the specimen is subjected to microwave energy from the microwave generator, which is tuned to a frequency (e.g. $\approx 10$ GHz) that is optimized for the specimen material. The microwave energy is coupled from the generator via a circulator toward a first side of the specimen using a coaxial cable fed microstrip antenna. The antenna preferably defines an opening through which excitation pulses from the laser source are directed toward the same first side of the specimen.

During the pulse duration, the laser excitation generates excess carriers that temporarily increase the local conductivity of the specimen, and then decay (when the pulse ends) until equilibrium within the specimen is again attained. When excess carrier concentration changes are small, the microwave reflectivity is proportional to the specimen's instantaneous conductivity. The optically induced change in carrier concentration, or specimen conductivity, measurably affects the microwave energy reflected by freed electrons and holes within the specimen. The reflected microwave energy is coupled from the antenna to the circulator, and then to a detector and associated means for processing for determining minority lifetime decay and associated specimen parameters.

According to the present invention, in an injection spectroscopic mode, the laser source energy preferably is varied between first and second power levels that can vary up to 1000:1. The ratio between these power levels is selected by the system operator according to the type of chemical impurity to be analyzed within the specimen. Where passivation is desired (e.g., for a non-oxidized specimen), the specimen is placed within an electrolyte bath to permit more accurate measurements of the internal structure of the specimen. Preferably the means for repositioning provides optical recognition of the flat portion of the specimen disk, and facilitates relative repositioning for rapid automated measurements.

Other features and advantages of the invention will appear from the following description in which the preferred embodiments have been set forth in detail in conjunction with the accompanying drawings.

DETAILED DESCRIPTION OF THE PREFERRED EMBODIMENTS

Figure 2:
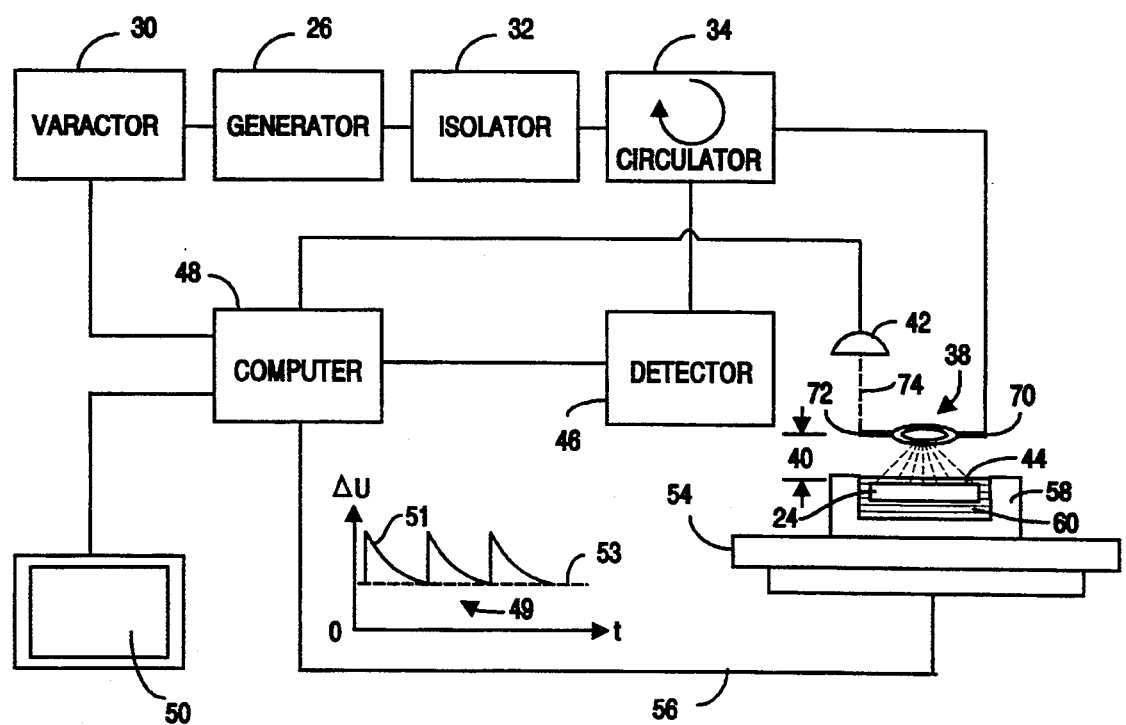
FIG. 2 depicts a preferred embodiment of the present invention.

As shown in FIG. 2, a system 22 for measuring minority carrier concentration in a semiconductor specimen 24 includes a microwave generator 26 whose oscillation frequency is tunable by varying a potential on a control lead 28 to a varactor 30. Preferably element 26 is a Gunn oscillator operable over a frequency range of about 10.2 GHz to about 10.45 GHz with an output power of about 100 mW, although other microwave generators also could be used. The output from oscillator 26 preferably is coupled to an isolator 32, to a circulator 34, and then via coaxial cable 36 to a tuned microstrip antenna 38. Preferably antenna 38 is narrowband and is disposed in near-field relation to the specimen 38. In a preferred embodiment, distance 40 is preferably less than 0.1 microwave wavelength or about 2 mm, and the specimen 24 acts as a termination impedance to the microwave path. The use of a narrowband tuned microstrip antenna in a near field system that includes the specimen as an impedance termination in the microwave path is in contrast to prior art systems. As noted, this configuration renders system 22 substantially immune to mechanical vibration of the specimen.

A pulsed source of laser excitation 42 creates minority carriers within the specimen 24, whose recombination lifetime affects microwave energy reflecting from free electrons and holes in the specimen. Microwave energy from antenna 38 is directed toward specimen surface 44, and the microwave energy thus reflected can characterize electron and hole recombination within the specimen. The reflected microwave energy is received by the antenna 38, then passes through the circulator 34 into a detector circuit 46 and preferably through a computer system 48 for further signal processing. The isolator 32 acts to prevent the reflected energy from passing through the circulator 34 back into the microwave generator 26.

The detector 46 preferably includes a Schottky diode and provides a voltage output signal, indicated as waveform 49 in FIG. 2. with the onset of each laser optical pulse, each detector output waveform 51 increases sharply in proportion to the change in conductivity ($\Delta u$) of the specimen. Waveform 49 then decays with a time constant proportional to the minority carrier recombination lifetime toward a baseline level 53. The baseline level 53 represents the essentially unmodulated constant or steady-state reflected microwave energy in the absence of photoexcitation from laser source 42. Typically system mechanical vibrations are below about 100 Hz, and preferably the detector 46 includes circuitry to filter out frequencies below 100 Hz, and to restore baseline 53 by integrating pulses 51 for a duration of many pulses, e.g., perhaps 1,000 pulses. Although as noted system 22 is substantially immune to vibration of specimen 22, rejecting detector output frequencies lower than about 100 Hz and providing an integrated baseline promotes system performance. Such filtering and integration circuits are well known to those in the art of circuit design and signal processing, and applicants therefore will not describe detector 46 and its associated circuitry in further detail.

Computer system 48 displays a variety of operator selectable information on video monitor 48 relating to impurities and their location within the specimen 24.

Computer system 48 preferably is an IBM PC AT or equivalent, and monitor 50 preferably has VGA resolution of at least 640×480 pixels.

As indicated by FIG. 2, the computer system 48 preferably controls the microwave oscillator frequency via control lead 28, controls the laser source 42 via control lead 52, and controls a table mechanism 54 via control lead 56 for controllably repositioning the specimen 24 relative to laser source 42 after each measurement. Optionally, system 22 permits measurements to be taken while a non-oxidized specimen 24 is placed within a container 58 that holds an electrolytic bath 60. As will be further described, bath 60 permits passivation of the various surfaces of the non-oxidized specimen to substantially reduce the detrimental effects of surface recombination upon the measurement process.

Laser source 42 preferably is a GaAs device, operating at a wavelength of about 904 nm with a power level controllable variable between about 25 mW and about 25 W, with a spot size of less than about 1 mm$^2$ at specimen surface 44. The effective injection level provided by such a laser device 42 is varied between about $5 \times 10^{13}$ to about $5 \times 10^{16}$ photon/cm$^3$s under control of the computer system 48 via control lead 52. Preferably laser 46 provides output pulses having a duration between about 100 ns to about 200 ns, and is operated at a low duty cycle with a repetition rate of about 1 Khz. Software used with computer system 48 allows the operator to select and control the laser pulse width, duty cycle, power levels and the like.

Figure 3A:
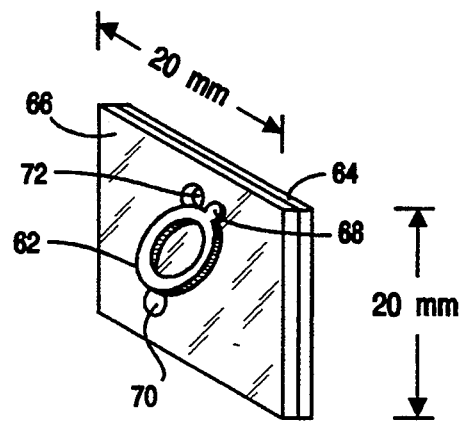
FIG. 3A depicts a microstrip antenna according to the present invention.
Figure 3B:
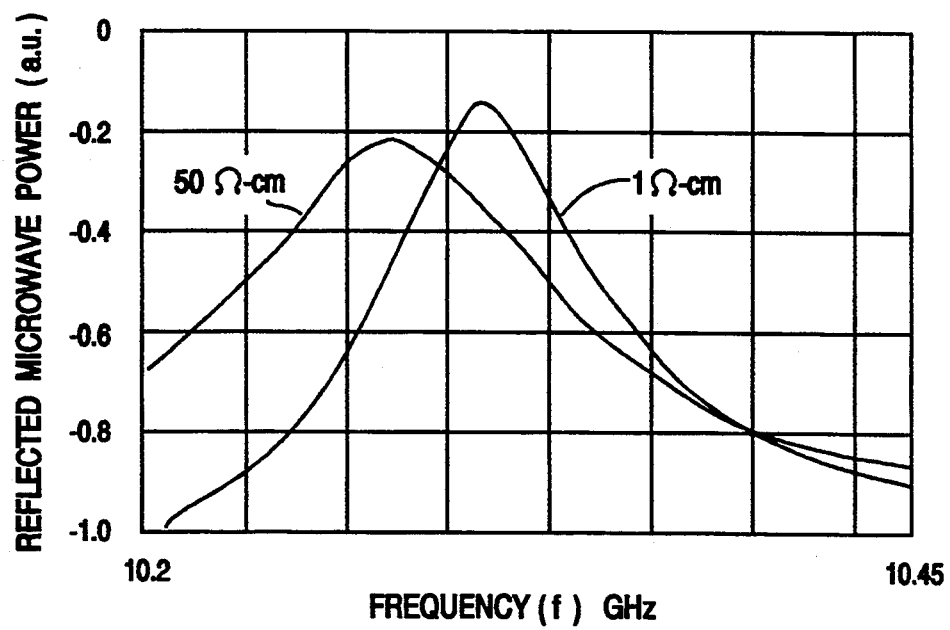
FIG. 3B is a graph of resonance characteristics for the microstrip antenna of FIG. 3B.

FIG. 3A is a detailed plan view of the narrowband tuned antenna 38, which preferably is a light weight, printed circuit microstrip antenna consisting of a copper ring strip 62 and a spaced apart ground plane metallization 64 (preferably measuring about 20 mm on each side), with a dielectric substrate 66 (e.g., teflon) therebetween. By "tuned", it is meant that the antenna resonant frequency is fixed by the antenna geometry at time of manufacture. Preferably the copper ring strip 62 includes a tuning stub 68 that may be dimensioned during printed circuit fabrication to yield an antenna having a desired resonant frequency. The antenna 38 preferably includes a microwave input connection point 70 (to which coaxial cable 38 is coupled), and an optical through hole 72, preferably diametrically opposite from point 70, at a location of maximum electric field. As shown in FIG. 2, optical excitation 74 from the pulsed laser source 42 passes through hole 72 to excite the same specimen surface 44 that is subjected to microwave energy from antenna 38. Applicants have found the ring shaped configuration of FIG. 3A to demonstrate excellent sensitivity and tunable frequency response. The resonance curves in FIG. 3B demonstrate the excellent narrow bandwidth provided by a tuned antenna 38 according to the present invention.

Figure 1:
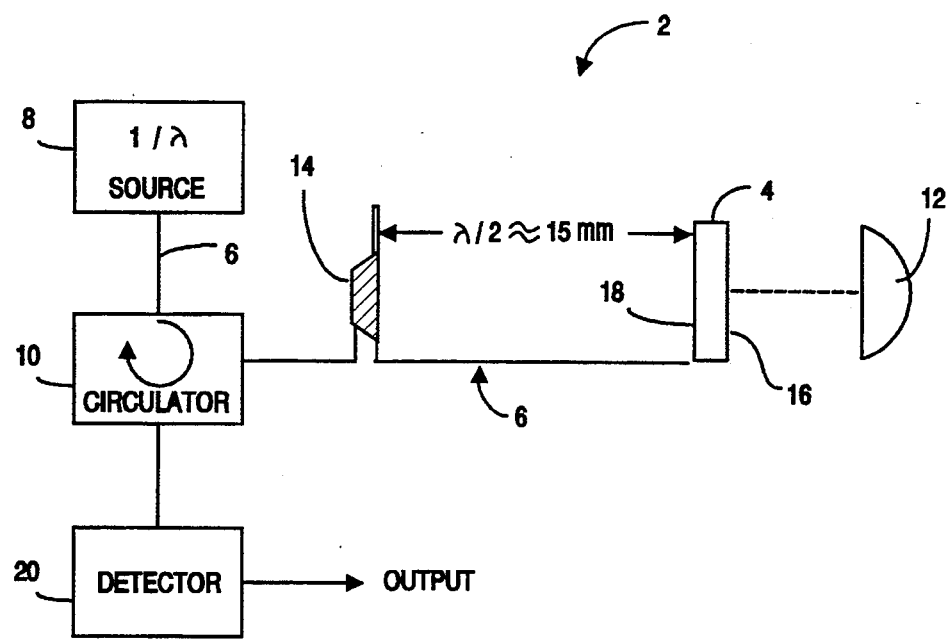
FIG. 1 depicts a prior art system for measuring minority carrier concentrations in a semiconductor specimen in a non-destructive, contact-free manner.

Unlike the prior art system of FIG. 1, the present system 22 is "one-sided" in that both microwave excitation from antenna 38 and optical excitation from laser 42 are directed toward a single specimen surface 44. The near field configuration of FIG. 2 is in further contrast to the prior art shown in FIG. 1 in that system 22 is tuned for maximum detector 48 output by varying the frequency of the microwave generator 26, preferably upon operator command of computer 48 via varactor 30. Unlike prior art systems, there is no need for additional metal reflectors or the like within the microwave field.

In systems such as those depicted in FIG. 1 and FIG. 2, the effective microwave field generated by an antenna decreases approximately inversely as the square of the distance from the antenna. Thus, comparing the typically 2 mm separation distance 40 in the present invention with the typically 15 mm separation distance in the prior art, it will be appreciated that the present invention subjects the specimen to a microwave field substantially greater than the field existing in the prior art configuration of FIG. 1. Further, because the tuned microstrip antenna 38 is substantially narrowband as contrasted with the open cavity configuration of FIG. 1, the present invention exhibits a signal/noise ratio substantially better than prior art systems. In further contrast to the prior art, because of the near field configuration used, specimen 24 effectively acts as an impedance termination for the microwave path and thus any vibration by specimen 24 will not significantly degrade measurements. As a result, computer system 48 can rapidly and automatically reposition specimen 24 by controlling table mechanism 54 such that system 22 makes measurements approximately fifty times more quickly than prior art systems.

Conventional wisdom has taught that a linear microwave response would not be provided unless $\Delta P/P < 0.03$, where P is microwave reflection and $\Delta P$ is the change in microwave reflection. This constraint has long dictated that a large microwave excitation volume should be provided. In reality, applicants have discovered that while this ratio should be minimized, it is sufficient if detectable $\Delta P$ is present, and that it is not necessary or even desirable to provide a large microwave excitation volume. A useful signal from the specimen is obtained primarily from the specimen volume subject to the laser excitation. In the preferred embodiment, the microwave spot at the specimen extends over an area of about 6 mm by about 8 mm, whereas the laser beam spot is about 1 mm$^2$. By contrast, prior art systems have a substantially larger ratio, because the wide area antenna system excites an overly large microwave volume, with resultant poor signal/noise.

Conventional wisdom has also instructed that a low laser excitation level was necessary for specimen recombination to be characterized by a single time constant $\Delta n/p$, which preferably was 0.01 or less, where $\Delta n$ is change in number of majority carriers, and p is the number of minority carriers. This consideration has long dictated that a large optical excitation volume be provided, but for classical minority carrier recombination analysis, a relatively low laser injection level is indicated. Prior art systems generally could not realize this ratio because their inherent microwave field insensitivity required a large laser injection level. Although applicants' system 22 is capable of operation at relatively low laser injection levels, the importance of this ratio appears to have been exaggerated in the literature. However applicants have discovered there can in fact be benefits to using both a low and a high laser injection level, especially where microwave reflectivity measurements are taken essentially simultaneously at both levels in an injection level spectroscopic mode.

As noted, prior art systems with their wide antenna radiation and relatively large distances between antenna and specimen exhibit poor microwave sensitivity that requires high power laser excitation. This requirement is especially severe for prior art systems where small resistivity specimens are to be examined because of the associated small microwave energy penetration. By contrast, the high microwave sensitivity realized by the present invention permits meaningful measurements to be taken with laser power levels varying from about 25 W (a power level similar to what is required in the prior art) to about 25 mW (a power level too low to provide meaningful measurement in the prior art). This large (e.g., about 1,000:1) dynamic range of laser injection facilitates injection spectroscopic measurements, even for small resistivity specimens.

In spectroscopic measurements, the system operator controls operation of the laser 42, using computer system 48. Recombination lifetime measurements are taken at preferably two or more laser power levels that are optimized for the chemical impurity under investigation within specimen 24. A ratio between measured high and low excitation level lifetimes provides a number that characterizes contaminants within the specimen.

More specifically, photoexcitation from laser 42 causes the simultaneous injection of electron-hole pairs in specimen 24, and recombination occurs at each deep level present within the specimen. This recombination process is inherently non-selective, and is governed by the Schottky-Read-Hall statistics. Conventional wisdom has taught that at low excitation level (e.g., p-type extrinsic material), minority carrier recombination lifetime is given by:

$$\tau_o \tau_{no} \quad (1)$$

where $\tau_{no} = (N_T \sigma_n v)^{-1}$, $N_T$ is the contaminant concentration, $\sigma_n$ is the electron capture cross-section, and v is drift velocity. However the above approximation is only valid for laser excitation values near midgap energy levels and for relatively high shallow doping concentrations.

For excitation levels near valence band levels in p-type material, the low excitation lifetime is better approximated by:

$$\tau_o = \tau_{no} \times e^{-[\frac{E_t - E_f}{k \times t}]} \quad (2)$$

where $E_t$ is the deep level activation energy measured from the valance band, and where $E_f$ is the Fermi energy. At room temperatures for a typical Fe-B contaminant, the above equation reduces to $\tau_o \approx 100 \tau_{no}$. Thus, in reality, even at low excitation levels that are nearer in energy to the band edge than to the Fermi level, $\tau_{no}$ is not actually being measured.

Applicants have discovered that a more meaningful analysis results if the specimen conductivity response function is examined at various levels of excess carrier injection. Injection level spectroscopic analysis is essentially the result of examinations made at at least two injection levels, preferably a relatively high level and a relatively low level. Prior art systems, with their inherent microwave insensitivity, are at best capable of high level, but not low level, laser excitation injection measurements. Such systems can evaluate the Schottky-Read-Hall equation only at the upper limit (e.g., high injection level), but not at both limits.

Thus, at high excitation limit, $$\tau_{oo} = \tau_{no} \tau_{po} \quad (3)$$

On one hand, a comparison of equations (1) and (3) demonstrates that for a typical midgap energy level, minority carrier lifetime decreases with decreasing injection level. On the other hand, it follows from equations (2) and (3) that minority carrier lifetime increases with decreasing injection level when the injection level is closer to the band edge than to the Fermi level. Using computer system 48 (or an equivalent computing system), these equations are preferably numerically calculated in their full and complete form, e.g., without limiting approximations. Because applicants' system provides accurate data both at high and low laser excitation energy levels, calculations based upon such data can provide more accuracy than calculations based upon data obtained from prior art systems. Applicants' tests using system 22 with various specimen containing Fe-B complex contaminants confirm these statements, and produce data in agreement with data in the literature. Applicants have confirmed, for example, that minority carrier lifetime resulting from high injection levels decreases with increasing Fe-B concentrations.

For shallower energy levels, the ratio:

$$I = \frac{\tau_{oo}}{\tau_o} = \left[1 + \frac{\sigma_p}{\sigma_n}\right] \times e^{[\frac{E_t - E_f}{kt}]} \quad (4)$$

may be tabulated for the typical transitional metal impurities (e.g., Fe-B, Cr, Au) in the doping level function. For a given temperature and doping level, equation (4) provides a characteristic number for each metallic impurity. Thus, in injection level spectroscopic mode, essentially simultaneous measurements are made for minority carrier recombination lifetime at low and at high laser excitation or injection levels. The ratio I, given by equation (4), is then formed from these two measurements, and is characteristic for a given contaminant. If several contaminants of comparable concentration levels are simultaneously present, an average number will be measured. However since it is unlikely that all contaminants will be present in the specimen in uniform concentration and distribution, a measurement of the ratio I over the specimen laterally should provide data separating and identifying the various contaminants.

It follows from equation (4) that the high to low injection level ratio I does not depend upon local contaminant content. Since relative change in minority carrier lifetime is investigated, the ratio I thus is not influenced by the distribution pattern of generated carriers.

Applicants' preferred method of injection level spectroscopic examination is to first measure standard high injection level minority carrier recombination lifetime to assess average contamination levels. Next the specimen is remeasured at low injection level, and the ratio I between measured high and low injection level lifetime is calculated and computer plotted as an "I Map", as depicted in FIG. 5 For a given impurity, I is a well defined number if free carrier concentration is known. Thus an "I Map" according to the present invention reveals the presence of different impurities by the different absolute values of I that correspond to the different contaminants.

With reference to FIG. 2, software within computer system 48 allows the system operator to specify which contaminants within specimen 24 should be examined. Via control lead 52, the computer system 48 will cause the laser source 42 to be excited at previously determined optimal high and low injection levels to produce good data for the contaminant under examination.

While a prior art system could provide measurement data at a high laser injection level, the microwave insensitivity inherent in such systems precludes substantially reducing the laser injection level.

The present invention permits mapping contaminant data as a function of specimen location, by preferably incrementally repositioning the specimen 24 between measurements relative to the laser source 42. The size of the repositioning increments may be operator selectable via computer system 48, which causes the table mechanism 54 to move via control lead 66. The resultant map, an exemplar of which is shown as FIG. 4A, may be produced on the monitor 50, may be plotted or printed out as depicted by FIG. 4B and 4C, as well as saved to persistent computer storage or to a floppy diskette.

Figure 4A:
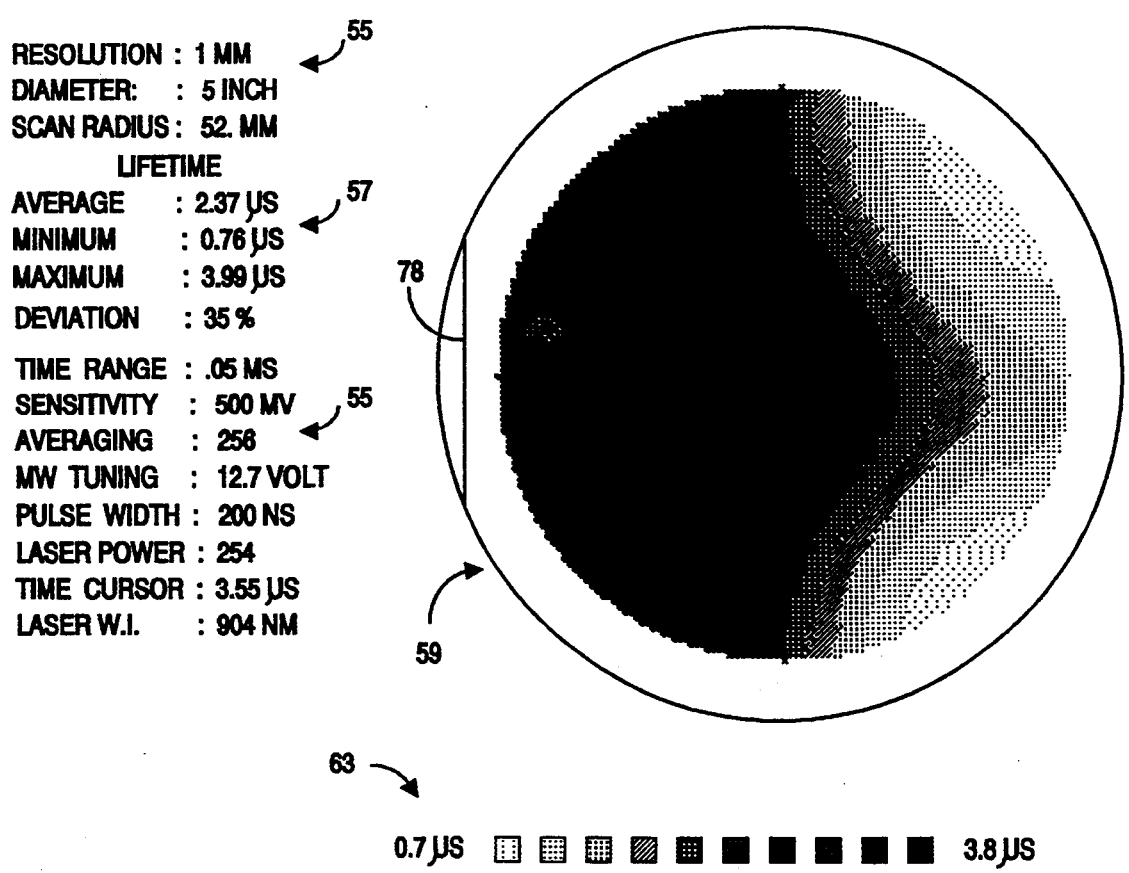
FIG. 4A depicts an actual computer generated parameter legend and display map of contaminant data as a function of specimen position, taken from monitor 50, according to the present invention.
Figure 4B:
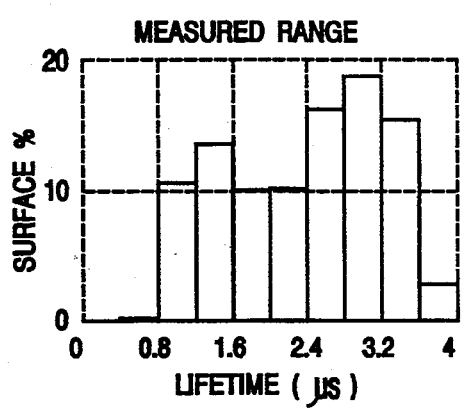
FIGS. 4B and 4C depict computer generated data plots, according to the present invention.
Figure 4C:
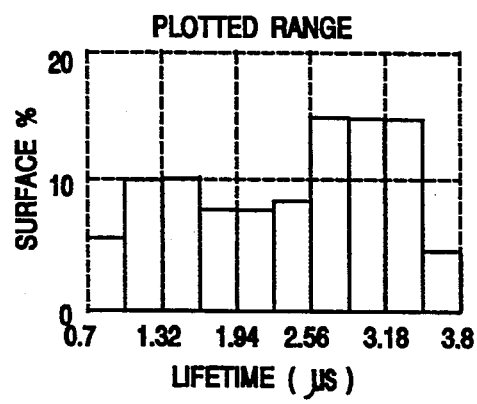

With reference to FIG. 4A, monitor 50 preferably displays certain operator selectable parameters 55, resultant minority carrier recombination lifetime data 57, a preferably multicolor plan view 59 of the specimen 24, and graphical representations 61 of measured and plotted lifetime data. A legend 63 permits the operator to determine from view 59 the recombination lifetime at any operator selected position on the specimen. The system software that creates the display shown in FIGS. 4A-4C flexibly permits other displays as well.

As noted, the "one-side" configuration of FIG. 2 advantageously provides the option of placing a nonoxidized specimen 24 within a bath 58 containing a surface passivating electrolyte 60. Preferably electrolyte 60 provides the equivalent of a simple chemical passivation of the electrically active surface sites in a non-oxidized specimen, and produces an almost ideal electrically inactive surface. Applicants have found, for example, that such passivation reduces surface recombination velocity on an oxide-free silicon specimen surface to about 0.3 cm/sec. For p-type silicon, electrolyte 60 preferably is 0.1 mol×dm$^{-3}$ NaF (pH<1), and for n-type silicon preferably the electrolyte is an alkaline solution >1 mol×dm$^{-3}$ NaOH and 25% $NH_3$. Other electrolytes and other concentrations could also be used.

Typically passivation suppresses surface recombination velocity to about 200–400 cm/sec, which corresponds to about 20–30 μs lifetime. Applicants' system 22 can measure the absolute value of recombination lifetime on a bare specimen (e.g., unpassivated and unoxidized) with an accuracy of about 1%, subject to the 20–30 μs surface recombination. While this represents a limitation as to absolute recombination accuracy, relative variations of defects within a specimen may be detected with a 1% accuracy using applicants' invention. As a result, even on a bare specimen, contaminants, oxygen precipitates and other lifetime limiting scattering sites whose limitation does not exceed about 1 ms can be resolved by applicants' invention. In various calibration tests, applicants have confirmed that system 22 when used with an electrolytic passivation bath 60 provides data for bare specimens that is consistent with data for chemically passivated specimens.

System 22 according to the present invention is controlled by computer system 48, which in turn is operated by software that preferably provides graphical user interface for ease of operation. After a specimen 24 is loaded into the table mechanism 54, it is optically scanned to determine the flat wafer orientation.

The system software provides initial menu choices, presented on video monitor 50. To scan and load a specimen, the operator selects a "Measure" menu, and then selects "Initialize". The software next seeks input list information, including sample name, file name, commend, date, operator identification. A "Load Wafer" menu selection is made and the system then looks for the specimen size, position and flat orientation. After this procedure is complete, recorded delay data are displayed by monitor 50.

Using a mouse, the operator is able to position a measuring head 76 that is coupled to detector 46 over a desired region of the specimen, whereupon a measurement is performed. Menu options invite the operator to select resolution of the defect map to be generated, e.g., 1, 2, 4, 8 mm, and the size of the wafer specimen, e.g., 4" (10.16 cm), 5" (12.7 cm), 6" (15.24 cm), 8" (20.32 cm). A "Prescan" menu choice allows display of decay curves. A "Measure" menu option provides a lifetime map display. Menu options also allow the map appearance to be altered so as to altered, to present data as a histogram for example. The various data and maps may be saved to disk or other storage, or printed.

The video display on monitor 50 allows for increase or decrease of transient recording time and voltage ranges, as well as laser excitation power, and microwave frequency. The video display provides an image of the scanned specimen, and the operator can position an image pointer within the image, using a computer mouse for example, where prescan measurements should be performed. Monitor 50 displays a minority carrier lifetime map, and local regions of the specimen can be mouse selected for display of the parameters pertaining to the region. The system software preferably includes an autosetting algorithm that provides the operator with a suggested set of initial parameters such as microwave tuning, sensitivity, time base, and the like.

Figure 5A:
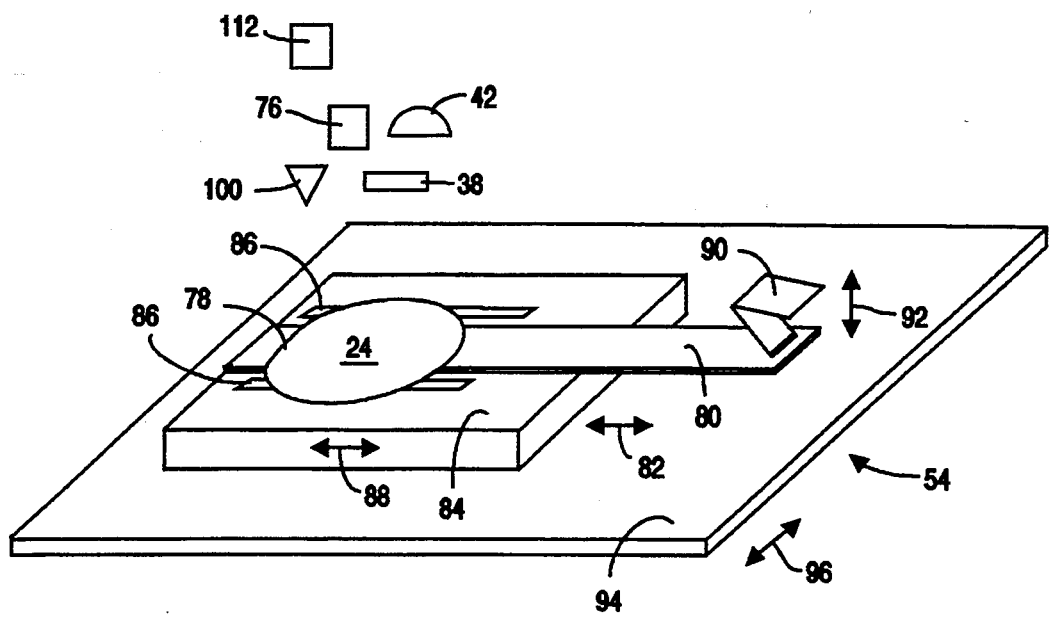
FIG. 5A depicts a specimen holding mechanism according to the present invention.

With reference to FIG. 5A, table mechanism 54 is shown in greater detail wherein specimen 24, which typically includes a flat indexing edge 78 is preferably vacuum mounted on a robotic slider arm 80. As indicated by arrow 82, arm 80 can move back and forth under control of computer system 48. Arm 80 in turn is disposed above and is preferably held against a table member 84 by a vacuum system indicated by element 86. Table member 84 is also capable of back and forth motion (indicated by arrow 88) under control of computer system 48.

Computer system 48 can cause arm 80 and table 84 to move together, for example when the specimen 24 is positioned on or of, or into or out of mechanism 54 by additional means (not shown in FIG. 5A). During a test period, preferably arm 80 is held stationary while table 84 moves, during which time a protective member 90, capable of relative vertical motion as indicated by arrow 92, protects arm 80. To minimize unwanted effects upon the microwave energy field, it is preferred that arm 80 and table member 54 are each formed from the same microwave inert material, plexiglass or teflon for example. Preferably a system table surface 94 disposed generally beneath arm 80 and table member 84 and capable of motion as shown by arrow 96 (under control of computer system 48) is made of the same material for the same reason.

Preferably under control of computer system 48, arm 80 and/or table member 84 and/or table surface 94 move incrementally relative to laser source 42. This relative movement causes substantially all regions of interest in specimen 24 to be subjected to microwave and optical energy respectively from antenna 38 and laser source 42. Thus, as detector 46 detects minority carrier recombination lifetime at various positions on specimen 24, a map (such as shown in FIG. 4) may be created displaying contaminants within the specimen.

Figure 5B:
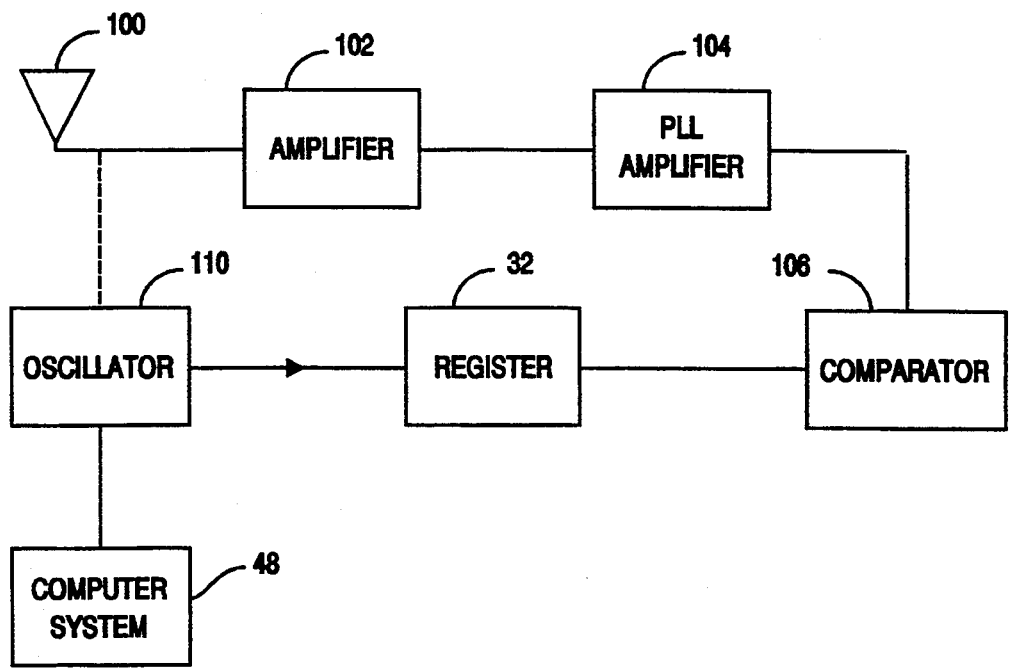
FIG. 5B depicts a mechanism for finding the edge of a wafer specimen, according to the present invention.

FIG. 5B (together with FIG. 5A) indicates generally how the edge 78 of the specimen wafer 24 is located, according to the present invention. A reflection optical-coupler mechanism 100, disposed generally over the specimen 24, preferably is controlled by a square wave frequency source whose frequency is about 1 KHz. The output from mechanism 100 is coupled to a selective amplifier 102, whose output in turn is coupled to a phase sensitive lock-in amplifier (e.g., a phase-lock loop amplifier) 104. A comparator 106 then converts the output of amplifier 104 to logic level that are provided to an output register 108. Register 108 also receives signals from oscillator 110, which in turn may also be used as the source of square waves for the optical-coupler mechanism 100. The above-described elements preferably operate under control of the computer system 48. A preferably linear camera 112, disposed over specimen 24, is coupled to the computer system 48 and the above-described elements to precisely detect the location and orientation of the flat edge 78 on the specimen.

While the present invention has been described with reference to a few specific embodiments, the description is illustrative of the invention and is not to be construed as limiting the invention. Various modifications may occur to those skilled in the art without departing from the true spirit and scope of the invention, as defined by the appended claims.

What is claimed is:

1. A system for characterizing defects in a semiconductor specimen having a first surface without contacting the specimen, the system comprising:
    a source of microwave energy;
    a tuned narrowband antenna coupled to said source for directing microwave energy toward said first surface, said antenna disposed in near field relationship to said first surface;
    a pulsed source of optical energy, disposed so as to radiate optical energy toward at least a portion of said first surface;
        said optical energy creating, within at least a region of said specimen, carrier pairs that begin to recombine upon cessation of each optical energy pulse;
    a detector coupled to said antenna for detecting microwave energy reflected by freed carriers in said specimen;
    wherein detected reflected microwave energy characterizes minority carrier recombination lifetime within said specimen and provides information as to defects therein.

2. The system of claim 1, wherein said antenna is a microstripline antenna.

3. The system of claim 2, wherein said antenna defines a through hole;
    said antenna being disposed such that optical energy from said pulsed source passes through said through hole enroute to said first surface.

4. The system of claim 2, wherein said antenna includes:
    a dielectric having first and second surfaces;
    a printed circuit conductive ring disposed on said first dielectric surface, said ring including a microwave coupling point for coaxial cable coupling said antenna to said source of microwave energy;
    a ground plane disposed on said second dielectric surface;
    said dielectric surface and ground plane defining a through hole disposed generally diametrically opposite said microwave coupling point;
    said antenna being disposed such that optical energy from said pulsed source passes through said through hole enroute to said first surface.

5. The system of claim 4, wherein said dielectric and said ground plane are substantially the same size, and have a length of about 20 mm.

6. The system of claim 1, wherein said antenna is disposed less than about 4 mm from said first surface of said specimen.

7. The system of claim 1, wherein said specimen comprises an impedance terminating a microwave path including said microwave source and antenna;
    wherein said terminated specimen substantially reduces system measurement error due to mechanical vibration of said specimen.

8. The system of claim 1, wherein said pulsed source of optical energy provides a power output selectable over a range of about 25 W to about 25 mW.

9. The system of claim 8, wherein minority carrier lifetime measurements are taken essentially simultaneously with said source of optical energy operating at a first, relatively high, power level, and at a second, relatively low, power level;
    a ratio of minority carrier recombination lifetime measurements taken at said first and second levels of optical energy yielding a number tending to identify at least one contaminant in said specimen.

10. The system of claim 1, further including a receptacle containing an electrolytic bath;
    a non-oxidized specimen being disposed within said receptacle during measurements such that said electrolytic bath passivates each surface of said specimen;
        said passivation substantially eliminating surface recombination thereby enabling the system to provide meaningful measurements for a non-oxidized specimen.

11. The system of claim 1, wherein said source of microwave energy is tunable to a frequency in the range of about 10.2 GHz to about 10.45 GHz such an output signal from said detector is optimized.

12. A system for characterizing defects in a semiconductor specimen having a first surface without contacting the specimen, the system comprising:
    a source of microwave energy tunable over a frequency within a range of about 10.1 GHz to about 10.45 GHz;
    a tuned narrowband microstrip antenna coupled to said source for directing microwave energy toward said first surface, said antenna disposed in near field relationship to said first surface;
    said antenna including:
        a dielectric having first and second surfaces;
        a printed circuit conductive ring disposed on said first dielectric surface, said ring including a microwave coupling point for coaxial cable coupling said antenna to said source of microwave energy;
        a ground plane disposed on said second dielectric surface;
        said dielectric surface and ground plane defining a through hole disposed generally diametrically opposite said microwave coupling point;

a pulsed source of optical energy, disposed so as to radiate optical energy through said though hole in said antenna toward at least a portion of said first surface;

said optical energy creating, within at least a region of said specimen, carrier pairs that begin to recombine upon cessation of each optical energy pulse;

a detector coupled to said antenna for detecting microwave energy reflected by freed carriers in said specimen;

wherein detected reflected microwave energy characterizes minority carrier recombination lifetime within said specimen and provides information as to defects therein.

13. The system of claim 12, wherein said antenna dielectric and said antenna ground plane are substantially the same size, and have a length of about 20 mm.

14. The system of claim 12, wherein said antenna is disposed less than about 4 mm from said first surface of said specimen.

15. The system of claim 12, wherein said specimen comprises an impedance terminating a microwave path including said microwave source and antenna;

wherein said terminated specimen substantially reduces system measurement error due to mechanical vibration of said specimen.

16. The system of claim 12, wherein:

said pulsed source of optical energy is a laser providing a power output selectable over a range of about 25 W to about 25 mW; and minority carrier lifetime measurements are taken essentially simultaneously with said source of optical energy operating at a first, relatively high, power level, and at a second, relatively low, power level;

a ratio of minority carrier recombination lifetime measurements taken at said first and second levels of optical energy yielding a number tending to identify at least one contaminant in said specimen.

17. The system of claim 12, further including a receptacle containing an electrolytic bath;

a non-oxidized specimen being disposed within said receptacle during measurements such that said electrolytic bath passivates each surface of said specimen;

said passivation substantially eliminating surface recombination thereby enabling the system to provide meaningful measurements for a non-oxidized specimen.

18. A method for characterizing defects in a semiconductor specimen having a first surface without contacting the specimen, the method comprising the following steps:

coupling a source of microwave energy to an narrow-band tuned antenna for directing microwave energy toward said first surface, said antenna being disposed in near field relationship to said first surface of said specimen;

providing a pulsed source of optical energy, disposed so as to radiate optical energy toward at least a portion of said first surface;

said optical energy creating within at least a region of said specimen carrier pairs that begin to recombine upon cessation of each optical energy pulse;

coupling a detector to said antenna for detecting microwave energy reflected by freed carriers in said specimen;

wherein said reflected microwave energy characterizes minority carrier recombination lifetime within said specimen and provides information as to defects therein.

19. The method of claim 18, wherein the specimen comprises an impedance termination for a microwave path including said source of microwave energy and said antenna.

20. The method of claim 18, wherein said antenna is a microstripline antenna comprising:

a dielectric having first and second surfaces;

a printed circuit conductive ring disposed on said first dielectric surface, said ring including a microwave coupling point for coaxial cable coupling said antenna to said source of microwave energy;

a ground plane disposed on said second dielectric surface;

said dielectric surface and ground plane defining a through hole disposed generally diametrically opposite said microwave coupling point;

said antenna being disposed such that optical energy from said pulsed source passes through said through hole enroute to said first surface.

21. The method of claim 18, wherein:

said pulsed source of optical energy provides a power output selectable over a range of about 25 W to about 25 mW; and minority carrier lifetime measurements are taken essentially simultaneously with said source of optical energy operating at a first, relatively high, power level, and at a second, relatively low, power level;

a ratio of minority carrier recombination lifetime measurements taken at said first and second levels of optical energy yielding a number tending to identify at least one contaminant in said specimen.

22. The method of claim 18, wherein said antenna is disposed less than about 4 mm from said first surface of said specimen.

23. The method of claim 18, further including the steps of:

placing a non-oxidized said specimen within a receptacle containing an electrolytic bath during measurement such that said electrolyte bath passivates each surface of said specimen;

said passivation substantially eliminating surface recombination thereby enabling the system to provide meaningful measurements for a non-oxidized specimen.

* * * * *